United States Patent
Guggenheim et al.

(10) Patent No.: US 10,435,511 B2
(45) Date of Patent: Oct. 8, 2019

(54) POLYETHERIMIDE OF IMPROVED COLOR AND PROCESS OF PREPARING

(71) Applicant: SABIC GLOBAL TECHNOLOGIES B.V., Bergen op Zoom (NL)

(72) Inventors: Thomas Link Guggenheim, Mt. Vernon, IN (US); Maria Patricia Forcen Jimenez, Murcia (ES); Javier Nieves Remacha, Madrid (ES); Bernabe Quevedo Sanchez, Murcia (ES); Juan Justino Rodriguez Ordonez, Murcia (ES)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/573,172

(22) PCT Filed: May 27, 2016

(86) PCT No.: PCT/US2016/034597
§ 371 (c)(1),
(2) Date: Nov. 10, 2017

(87) PCT Pub. No.: WO2016/196268
PCT Pub. Date: Dec. 8, 2016

(65) Prior Publication Data
US 2018/0127546 A1 May 10, 2018

(30) Foreign Application Priority Data
May 29, 2015 (EP) ..................... 15382288

(51) Int. Cl.
C08G 73/10 (2006.01)
B01F 7/00 (2006.01)
C07C 39/235 (2006.01)
C08F 2/01 (2006.01)
C08F 2/38 (2006.01)
C08L 79/08 (2006.01)

(52) U.S. Cl.
CPC ...... C08G 73/1003 (2013.01); B01F 7/00275 (2013.01); B01F 7/00291 (2013.01); C07C 39/235 (2013.01); C08F 2/01 (2013.01); C08F 2/38 (2013.01); C08G 73/1046 (2013.01); C08G 73/1053 (2013.01); C08L 79/08 (2013.01); B01F 2215/0036 (2013.01); C08F 2400/02 (2013.01)

(58) Field of Classification Search
CPC ............ C08G 73/1046; C08G 73/1053; C08G 73/1071
See application file for complete search history.

(56) References Cited

U.S. PATENT DOCUMENTS

| | | |
|---|---|---|
| 4,276,232 A | 6/1981 | Rasberger |
| 4,330,666 A | 5/1982 | White et al. |
| 4,520,204 A | 5/1985 | Evans |
| 4,988,544 A | 1/1991 | Cella et al. |
| 5,229,482 A | 7/1993 | Brunelle |
| 5,290,945 A | 3/1994 | Roy et al. |
| 5,608,027 A | 3/1997 | Crosby et al. |
| 6,235,866 B1 | 5/2001 | Khouri et al. |
| 6,265,521 B1 | 7/2001 | Fyvie et al. |
| 6,753,365 B2 | 6/2004 | Brown et al. |
| 6,919,418 B2 | 7/2005 | Khouri et al. |
| 7,842,824 B2 | 11/2010 | Mikami et al. |
| 8,080,671 B2 | 12/2011 | Guggenheim et al. |
| 8,299,204 B2 | 10/2012 | Germroth et al. |
| 8,354,491 B2 | 1/2013 | Crawford et al. |
| 8,372,941 B2 | 2/2013 | Bernabe et al. |
| 2003/0225194 A1 | 12/2003 | Coffy et al. |
| 2007/0225479 A1 | 9/2007 | Silvi et al. |
| 2008/0262196 A1 | 10/2008 | Giammattei et al. |
| 2009/0163691 A1 | 6/2009 | Bernabe et al. |
| 2009/0292128 A1 | 11/2009 | Guggenheim et al. |
| 2011/0263760 A1 | 10/2011 | Jakupca et al. |
| 2011/0263791 A1 | 10/2011 | Chiong et al. |
| 2013/0260125 A1 | 10/2013 | Ordonez et al. |
| 2013/0344313 A1 | 12/2013 | Ordonez et al. |
| 2014/0094535 A1 | 4/2014 | Guggenheim et al. |
| 2014/0099510 A1* | 4/2014 | Chiong ................ C07D 209/48 428/473.5 |
| 2018/0037699 A1 | 2/2018 | Guggenheim et al. |
| 2018/0044474 A1 | 2/2018 | Guggenheim et al. |

FOREIGN PATENT DOCUMENTS

| | | |
|---|---|---|
| EP | 2644640 A1 | 10/2013 |
| EP | 2644641 A1 | 10/2013 |
| GB | 2280183 A | 1/1995 |
| WO | 2009143440 A1 | 11/2009 |

OTHER PUBLICATIONS

International Search Report for International Application No. PCT/US2016/034597, International Filing Date May 27, 2016, dated Aug. 10, 2016, 6 pages.
Written Opinion for International Application No. PCT/US2016/034597 International Filing Date May 27, 2016, dated Aug. 10, 2016, 6 pages.

* cited by examiner

*Primary Examiner* — Kuo Liang Peng
(74) *Attorney, Agent, or Firm* — Cantor Colburn LLP

(57) ABSTRACT

A polyetherimide of improved color and processes for preparing the polyetherimide are disclosed.

19 Claims, 3 Drawing Sheets

POLYETHERIMIDE OF IMPROVED COLOR AND PROCESS OF PREPARING

This application is a national stage application of PCT/US2016/034597 filed May 27, 2016, which claims priority to European Patent Application Number 15382288.7 filed May 29, 2015, both of which are hereby incorporated by reference in their entirety.

BACKGROUND

To meet the increased demand for polyetherimide, a new process was invented with a new chemistry route called the displacement polymerization process. Synthesis of polyetherimide via the displacement polymerization route generally includes imidization (e.g., U.S. Pat. No. 6,235,866), diphenolic salt synthesis (e.g., U.S. Pat. No. 4,520,204) and polymerization (U.S. Pat. No. 6,265,521), followed by the downstream activities. In a specific embodiment of the displacement polymerization process, the bisimide resulting from the reaction of 2 moles of a chloro-substituted phthalic anhydride and 1 mole of metaphenylene diamine (the adduct abbreviated ClPAMI) polymerizes with bisphenol A disodium salt (BPANa₂) in the presence of a phase transfer catalyst, such as hexaethylguanidinium chloride (HEGCl). HEGCl is a well-known phase transfer catalyst to make polyetherimides. Utilization of HEGCl as a phase transfer catalyst at higher temperatures is described in U.S. Pat. No. 5,229,482.

It is desirable to improve the color quality (measured as Yellowness Index, or "YI") of the polyetherimide made by the displacement polymerization route. High color polymer requires more pigments and dyes to meet many color specifications, and the addition of excess colorants can result in loss of other polymer physical properties. A low base polymer color is therefore desirable.

There is an ongoing, unmet need for polyetherimides made by the displacement polymerization route having improved color properties, and methods of making such chloro-substituted polyetherimides.

SUMMARY

A method for the manufacture of a polyetherimide composition is disclosed, the method comprising contacting a bis(phthalimide) having the formula

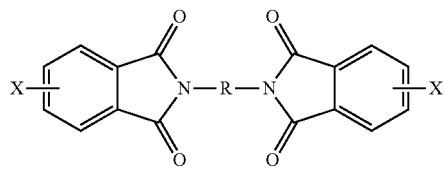

with an alkali metal salt of a dihydroxy aromatic compound having the formula MO—Z—OM, in an oil-jacketed reactor, in the presence of a catalyst and 0 to 10% of a capping agent, and at an oil temperature of 150° C. to 320° C., to form the polyetherimide comprising the structural units having the formula

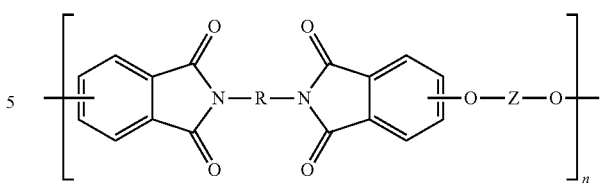

wherein in the foregoing formulae X is fluoro, chloro, bromo, iodo, nitro or a combination thereof; R is an aromatic hydrocarbon group having 6 to 27 carbon atoms, a halogenated derivative thereof, a straight or branched chain alkylene group having 2 to 10 carbon atoms, a halogenated derivative thereof, a cycloalkylene group having 3 to 20 carbon atoms, a halogenated derivative thereof, —($C_6H_{10}$)$_z$— wherein z is an integer from 1 to 4, an aromatic hydrocarbyl moiety having from 1 to 6 aromatic groups, and a divalent group of the formula

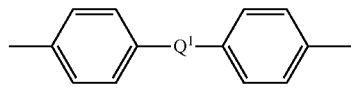

wherein $Q^1$ is —O—, —S—, —C(O)—, —SO₂—, —SO—, —$C_yH_{2y}$— wherein y is an integer from 1 to 5, or a combination thereof; M is an alkali metal; Z is an aromatic $C_{6-24}$ monocyclic or polycyclic moiety optionally substituted with 1 to 6 $C_{1-8}$ alkyl groups, 1 to 8 halogen atoms, or a combination thereof; and n is an integer greater than 1; and wherein the polyetherimide has a Yellowness Index of less than 93 to 50.

Also disclosed is a low color polyetherimide composition prepared via the displacement reaction from a substituted phthalic anhydride and an organic diamine at a temperature of 185° C. to 195° C. and mixing the reactor using an agitator with two sets of pitched turbine blades, with a blade to vessel diameter ratio range of about 0.45 to 0.65, at a speed in a range from about 40 to about 90 revolutions per minute, in a reactor with a volume range from about 20 to 35 cubic meters, and a cylindrical height to diameter ratio range of about 1.3 to about 1.6; or in another embodiment, wherein the agitator has two sets of 45° pitched turbine blades with a blade to vessel diameter ratio of about 0.54 at a speed in a range from about 70 to about 86 revolutions per minute in a reactor with volume of about 28 cubic meters with a cylindrical height to diameter ratio of about 1.45, wherein the polyetherimide has a Yellowness Index of less than 93, or less than 80, or less than 70. The polyetherimide can have a Yellowness Index of as low as 50.

A low color polyetherimide composition is disclosed, prepared via a displacement reaction from a substituted phthalic anhydride and an organic diamine in which the polymerization is quenched with an acid at a temperature of from 145° C. to 155° C., wherein the polyetherimide has a Yellowness Index of less than 93, or less than 80, or less than 70, or as low as 50.

A method for the manufacture of a polyetherimide composition is disclosed, the method comprising: contacting a bis(phthalimide) having the formula

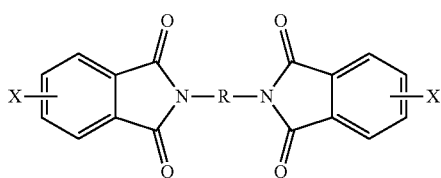

with an alkali metal salt of a dihydroxy aromatic compound having the formula MO—Z—OM, in an oil-jacketed reactor, in the presence of a catalyst and 0 to 10% of a capping agent, and at an oil temperature of 150° C. to 320° C., and mixing the reactor using an agitator with two sets of pitched turbine blades, with a blade to vessel diameter ratio range of about 0.45 to 0.65, at a speed in a range from about 40 to about 90 revolutions per minute, in a reactor with a volume range from about 20 to 35 cubic meters, and a cylindrical height to diameter ratio range of about 1.3 to about 1.6, quenching the polymerization with an acid at a temperature of from 130° C. to 200° C., to form a polyetherimide comprising structural units having the formula

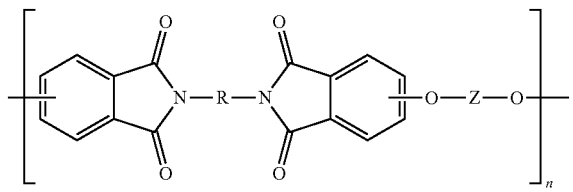

wherein in the foregoing formulae, X is fluoro, chloro, bromo, iodo, nitro, or a combination thereof; R is an aromatic hydrocarbon group having 6 to 27 carbon atoms, a halogenated derivative thereof, a straight or branched chain alkylene group having 2 to 10 carbon atoms, a halogenated derivative thereof, a cycloalkylene group having 3 to 20 carbon atoms, a halogenated derivative thereof, —$(C_6H_{10})_z$— wherein z is an integer from 1 to 4, an aromatic hydrocarbyl moiety having from 1 to 6 aromatic groups, and a divalent group of the formula

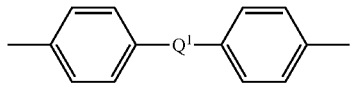

wherein $Q^1$ is —O—, —S—, —C(O)—, —$SO_2$—, —SO—, —$C_yH_{2y}$— wherein y is an integer from 1 to 5, or a combination thereof; M is an alkali metal; Z is an aromatic $C_{6-24}$ monocyclic or polycyclic moiety optionally substituted with 1 to 6 $C_{1-8}$ alkyl groups, 1 to 8 halogen atoms, or a combination thereof; and n is an integer greater than 1; and wherein the polyetherimide has a Yellowness Index of from less than 93 to 50.

These and other features, aspects, and advantages will become better understood with reference to the following description and appended claims.

DETAILED DESCRIPTION

Figure 1:
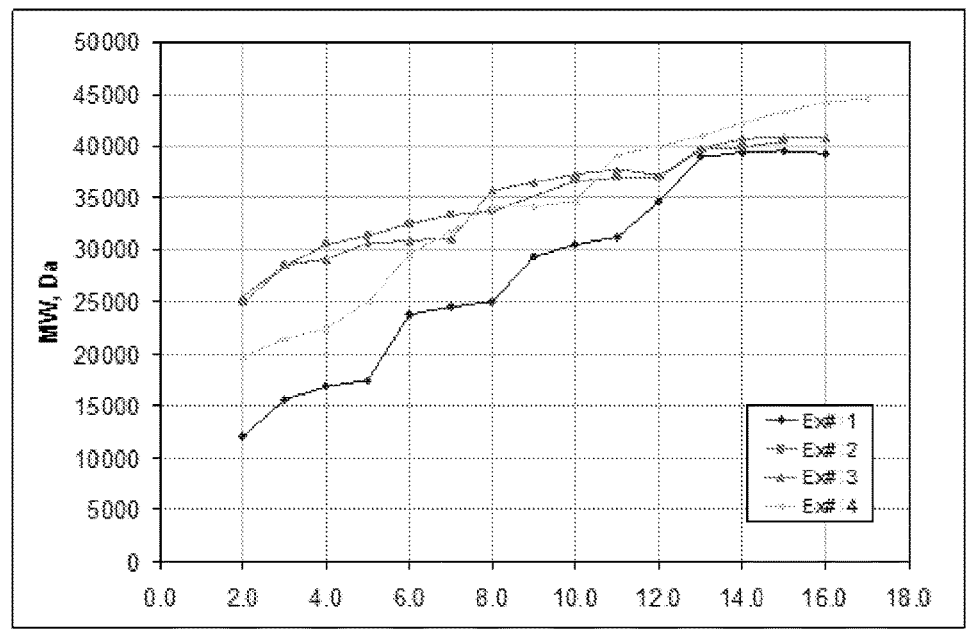
FIG. 1 is a graph of the Mw versus time profiles for Examples 1-4.

Downstream in the process of manufacturing a polyetherimide, the polymer is quenched with an acid such as phosphoric acid, in order to convert (via acidification) any remaining sodium phenoxide groups on the polymer chain into phenolic groups and sodium carboxylate groups into carboxylic acids. This ensures that there are no reactive groups remaining on the polymer chain, which can impact negatively the efficiency of polymer filtration and washing. The acid quench can be performed for a time of 15 to 360 minutes, or, more specifically, 20 to 40 minutes, or, even more specifically, 25 to 35 minutes.

The invention provides an improved process which lowers the acid quenching temperature and improves color, measured by YI. There is an improvement of YI by decreasing the temperature from 170° C. to 150° C., in another embodiment, the oil temperature is from about 145° C. to about 155° C.

Controlling the reaction conditions during polymerization, specifically wall temperature and agitation, affects the final polymer yellowness index (YI) and Mz/Mw. The mildest conditions (high speed agitation, and lower hot oil temperature) surprisingly gave a significantly lower YI as well as a significantly lower ratio of z-average molecular weight to weight average molecular weight (Mz/Mw). In some embodiments, the reactor is heated using a jacket where hot oil circulates at a temperature in a range from about 150° C. to about 320° C. In another embodiment, the reactor is heated using a jacket where hot oil circulates at a temperature in a range from about 180° C. to about 240° C., in another embodiment from 188° C. to 192° C.

Heat transfer in the commercial reactor from the heated jacket to the reaction mass is determined by a series of mechanisms: convective transfer by the hot oil flow in the jacket, conduction within the metal wall and convective transfer in the reactor volume. The largest resistance is given by the heat transfer from the wall to the bulk of the reactor volume. And this resistance is greatly impacted by the agitation in the reactor. The better the agitation, the higher the heat transfer per square meter for a given temperature gradient. Consequently, with poor mixing the hot oil temperature must be increased in order to achieve the desired heat flux. Conversely, enhanced mixing enables a reduction of the hot oil temperature while maintaining the desired heat flux.

In a non-homogeneous mixture, for example slurry contained in an agitated reactor, mixing needs to be sufficient to improve homogeneity, improve heat transfer, and avoid stagnation points on the vessel walls and agitator shafts. If the reactor is operated with too low agitation, for example, the volume of stagnant zones can increase and poor mass transfer is expected. Conversely, too high agitation speed can create a vortex around the agitator shaft, reduce the effective reaction volume, and produce excessive sidewall splash.

In a reactor, the interactions between substance properties (density, viscosity), agitator design, kinetics of reaction, and operating variables (agitator tip speed, wall temperature) can influence the extent of side reactions and therefore impact the final product properties.

In some embodiments, the reactor is mixed using an agitator with two sets of pitched turbine blades, with a blade to vessel diameter ratio range of about 0.45 to 0.65, at a speed in a range from about 40 to about 90 revolutions per minute, in a reactor with a volume range from about 20 to 35 cubic meters, and a cylindrical height to diameter ratio range of about 1.3 to about 1.6. In an another embodiment, the reactor is mixed using an agitator with two sets of 45° pitched turbine blades with a blade to vessel diameter ratio of about 0.54 at a speed in a range from about 70 to about 86 revolutions per minute in a reactor with volume of about 28 cubic meters with a cylindrical height to diameter ratio of about 1.45.

The polyetherimides are of formula (1)

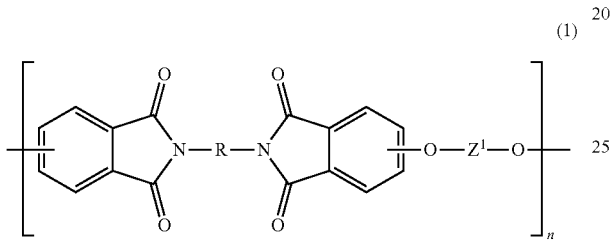

(1)

wherein n is greater than 1, for example, 10 to 1,000 or more, or more specifically 10 to 50; or for example 2 to 1000, or 5 to 500, or 10 to 100.

The group R in formula (1) is independently the same or different, and is a substituted or unsubstituted divalent organic group, for example, an aromatic hydrocarbon group having 6 to 27 carbon atoms, a halogenated derivative thereof, a straight or branched chain alkylene group having 2 to 10 carbon atoms, a halogenated derivative thereof, a cycloalkylene group having 3 to 20 carbon atoms, a halogenated derivative thereof, —($C_6H_{10}$)$_z$— wherein z is an integer from 1 to 4, an aromatic hydrocarbyl moiety having from 1 to 6 aromatic groups, or a divalent group of the formula (2)

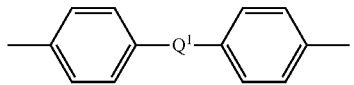

wherein $Q^1$ is —O—, —S—, —C(O)—, —SO$_2$—, —SO—, —$C_yH_{2y}$— wherein y is an integer from 1 to 5, or a combination thereof. In some embodiments R is divalent group of one or more of the following formulas (2a)

(2a)

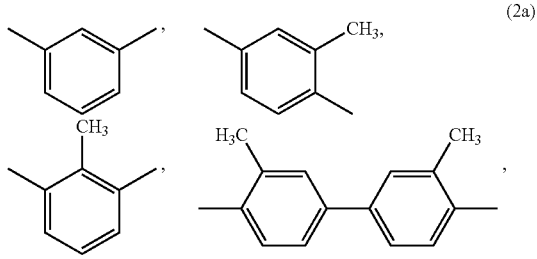

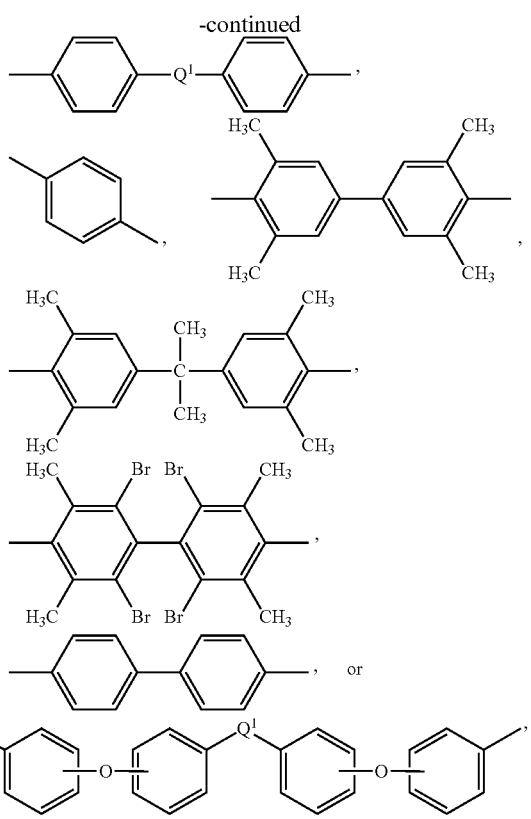

wherein $Q^1$ is —O—, —S—, —C(O)—, —SO$_2$—, —SO—, —$C_yH_{2y}$— wherein y is an integer from 1 to 5 or a halogenated derivative thereof (which includes perfluoro-alkylene groups), or —($C_6H_{10}$)$_z$— wherein z is an integer from 1 to 4. In some embodiments R is m-phenylene, p-phenylene, or a diarylene sulfone, in particular bis(4,4'-phenylene)sulfone, bis(3,4'-phenylene)sulfone, bis(3,3'-phenylene)sulfone, or a combination comprising at least one of the foregoing. In some embodiments, at least 10 mole percent of the R groups contain sulfone groups, and in other embodiments no R groups contain sulfone groups.

Further in formula (1), the divalent bonds of the —O—Z—O— group are in the 3,3',3,4',4,3', or the 4,4' positions, and Z is an aromatic $C_{6-24}$ monocyclic or polycyclic moiety optionally substituted with 1 to 6 $C_{1-8}$ alkyl groups, 1 to 8 halogen atoms, or a combination comprising at least one of the foregoing, provided that the valence of Z is not exceeded. Exemplary groups Z include groups of formula (3)

(3)

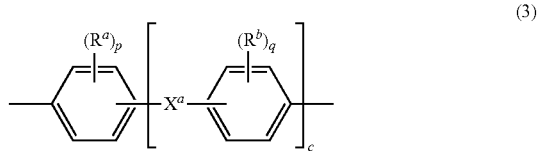

wherein $R^a$ and $R^b$ are each independently the same or different, and are a halogen atom or a monovalent $C_{1-6}$ alkyl group, for example; p and q are each independently integers of 0 to 4; c is 0 to 4; and $X^a$ is a bridging group connecting the hydroxy-substituted aromatic groups, where the bridging group and the hydroxy substituent of each $C_6$ arylene group are disposed ortho, meta, or para (specifically para) to each other on the $C_6$ arylene group. The bridging group $X^a$ can be a single bond, —O—, —S—, —S(O)—, —S(O)$_2$—, —C(O)—, or a $C_{1-18}$ organic bridging group. The $C_{1-18}$ organic bridging group can be cyclic or acyclic, aromatic or non-aromatic, and can further comprise heteroatoms such as halogens, oxygen, nitrogen, sulfur, silicon, or phosphorous. The $C_{1-18}$ organic group can be disposed such that the $C_6$ arylene groups connected thereto are each connected to a common alkylidene carbon or to different carbons of the $C_{1-18}$ organic bridging group. A specific example of a group Z is a divalent group of formula (3a)

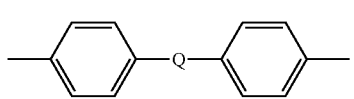
(3a)

wherein Q is —O—, —S—, —SO$_2$—, —SO—, or —C$_y$H$_{2y}$— wherein y is an integer from 1 to 5 or a halogenated derivative thereof (including a perfluoroalkylene group). In a specific embodiment Z is a derived from bisphenol A, such that Q in formula (3a) is 2,2-isopropylidene.

In another embodiment, the polyetherimide comprises more than 1, specifically 10 to 1,000, or more specifically, 10 to 50 structural units, of formula (1) wherein R is a divalent group of formulas (3) wherein $Q^1$ is —C$_y$H$_{2y}$— wherein y is an integer from 1 to 5 or a halogenated derivative thereof, and Z is a group of formula (4a). In some embodiments, R is m-phenylene, p-phenylene, p-arylene diphenylsulfone, or a combination thereof, and $Z^1$ is 2,2-(4-phenylene)isopropylidene. An example of a polyetherimide sulfone comprises structural units of formula (1) wherein at least 50 mole percent of the R groups are of formula (2) wherein Q is —SO$_2$— and the remaining R groups are independently p-phenylene or m-phenylene or a combination comprising at least one of the foregoing; and $Z^1$ is 2,2-(4-phenylene) isopropylidene.

In some embodiments, the polyetherimide is a copolymer that optionally comprises additional structural imide units that are not polyetherimide units, for example imide units of formula (4)

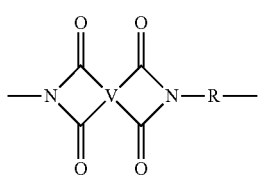
(4)

wherein R is as described in formula (1) and each V is the same or different, and is a substituted or unsubstituted $C_{6-20}$ aromatic hydrocarbon group, for example a tetravalent linker of the formulas

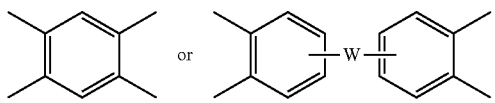

wherein W is a single bond, —S—, —SO$_2$—, —SO—, or —C$_y$H$_{2y}$— wherein y is an integer from 1 to 5 or a halogenated derivative thereof (which includes perfluoroalkylene groups). These additional structural imide units preferably comprise less than 20 mol % of the total number of units, and more preferably can be present in amounts of 0 to 10 mol % of the total number of units, or 0 to 5 mol % of the total number of units, or 0 to 2 mole % of the total number of units. In some embodiments, no additional imide units are present in the polyetherimide.

The polyetherimides are prepared by the so-called "displacement" method. In this method, a substituted phthalic anhydride of formula (7)

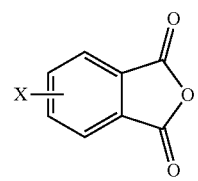
(7)

wherein X is a halogen or a nitro group, is condensed (imidized) with an organic diamine of the formula (8)

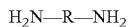
H$_2$N—R—NH$_2$ (8)

wherein R is as described in formula (1), to form a bis (phthalimide) of formula (9).

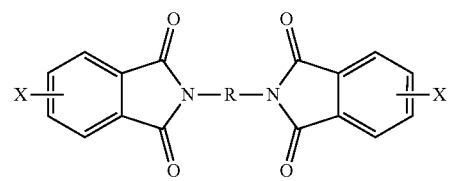
(9)

In some embodiments, X is a halogen, specifically fluoro, chloro, bromo, or iodo, or X is nitro. Preferably X is a halogen to provide a bis(halophthalimide), more preferably chloro to provide bis(chlorophthalimide). A combination of different X groups, preferably halogens, can be used.

Illustrative examples of amine compounds of formula (8) include 1,4-butane diamine, 1,5-pentanediamine, 1,6-hexanediamine, 1,7-heptanediamine, 1,8-octanediamine, 1,9-nonanediamine, 1,10-decanediamine, 1,12-dodecanediamine, 1,18-octadecanediamine, 3-methylheptamethylenediamine, 4,4-dimethylheptamethylenediamine, 4-methylnonamethylenediamine, 5-methylnonamethylenediamine, 2,5-dimethylhexamethylenediamine, 2,5-dimethylheptamethylenediamine, 2, 2-dimethylpropylenediamine, N-methyl-bis (3-aminopropyl) amine, 3-methoxyhexamethylenediamine, 1,2-bis(3-aminopropoxy) ethane, bis(3-aminopropyl) sulfide, 1,4-cyclohexanediamine, bis-(4-aminocyclohexyl) methane, m-phenylenediamine, p-phenylenediamine, 2,4-diaminotoluene, 2,6-diaminotoluene, m-xylylenediamine, p-xylylenediamine, 2-methyl-4,6-diethyl-1,3-phenylene-diamine, 5-methyl-4,6-diethyl-1,3-phenylene-diamine, benzidine, 3,3'-dimethylbenzidine, 3,3'-dimethoxybenzidine, 1,5-diaminonaphthalene, bis(4-aminophenyl) methane, bis(2-chloro-4-amino-3, 5-diethylphenyl) methane, bis(4-aminophenyl) propane, 2,4-bis(b-amino-t-butyl) toluene, bis(p-b-amino-t-butylphenyl) ether, bis(p-b-methyl-o-aminophenyl) benzene, bis(p- b-methyl-o-aminopentyl) benzene, 1, 3-diamino-4-isopropylbenzene, bis(4-aminophenyl) ether and 1,3-bis(3-aminopropyl) tetramethyldisiloxane. Mixtures of these amines can be used. Illustrative examples of amine compounds of formula (8) containing sulfone groups include 4,4'-diamino diphenyl sulfone (DDS) and bis(aminophenoxy phenyl) sulfones (BAPS). Any regioisomer of the foregoing compounds can be used. $C_{1-4}$ alkylated or poly($C_{1-4}$)alkylated derivatives of any of the foregoing can be used, for example a polymethylated 1,6-hexanediamine Combinations comprising any of the foregoing amines can be used.

Specifically, diamine (8) is a meta-phenylene diamine (8a) or a para-phenylene diamine (8b)

(8a)

(8b)

wherein $R^a$ and $R^b$ are each independently a halogen atom, nitro, cyano, $C_2$-$C_{20}$ aliphatic group, $C_2$-$C_{40}$ aromatic group, and a and b are each independently 0 to 4. Examples include meta-phenylenediamine (mDA), para-phenylenediamine (pDA), 2,4-diaminotoluene, 2,6-diaminotoluene, 2-methyl-4,6-diethyl-1,3-phenylenediamine, 5-methyl-4,6-diethyl-1,3-phenylenediamine, 1,3-diamino-4-isopropylbenzene, and 4,4'-diamino diphenyl sulfone. In some embodiments, diamine (8) is meta-phenylene diamine, para-phenylene diamine, 4,4'-diamino diphenyl sulfone, and a combination thereof.

Condensation of substituted phthalic anhydride (7) and diamine (8) (imidization) can be conducted in the absence or presence of a catalyst.

The reaction is generally conducted in the presence of a relatively non-polar solvent, preferably with a boiling point above 100° C., specifically above 150° C., for example, o-dichlorotoluene, dichlorotoluene, 1,2,4-trichlorobenzene, diphenyl sulfone, a monoalkoxybenzene such as anisole, veratrole, diphenylether, or phenetole. Ortho-dichlorobenzene and anisole can be particularly mentioned.

The bis(phthalimide)s (9) are generally prepared at least 110° C., specifically 150° C. to 275° C., more specifically 175° C. to 225° C. At temperatures below 110° C., reaction rates may be too slow for economical operation. Atmospheric or super-atmospheric pressures can be used, for example, up to 5 atmospheres, to facilitate the use of high temperatures without causing solvent to be lost by evaporation.

The solvent, diamine (8), and substituted phthalic anhydride (7) can be combined in amounts such that the total solids content during the reaction to form bis(phthalimide) (9) does not exceed 25 wt. %, or 17 wt. %. "Total solids content" expresses the proportion of the reactants as a percentage of the total weight, including liquids, present in the reaction at any given time.

In general practice, a molar ratio of substituted phthalic anhydride (7) to diamine (8) of 1.98:1 to 2.2:1, specifically 1.98:1 to 2.1, or about 2:1 is used. According to the invention a slight excess of anhydride is desired to improve the color of the final product. A proper stoichiometric balance between substituted phthalic anhydride (7) and diamine (8) is maintained to prevent undesirable by-products that can limit the molecular weight of the polymer, and/or result in polymers with amine end groups. Accordingly, in some embodiments, imidization proceeds adding diamine (8) to a mixture of substituted phthalic anhydride (7) and solvent to form a reaction mixture having a targeted initial molar ratio of substituted phthalic anhydride to diamine; heating the reaction mixture to a temperature of at least 100° C. (optionally in the presence of an imidization catalyst); analyzing the molar ratio of the heated reaction mixture to determine the actual initial molar ratio of substituted phthalic anhydride (7) to diamine (8); and, if necessary, adding substituted phthalic anhydride (7) or diamine (8) to the analyzed reaction mixture to adjust the molar ratio of substituted phthalic substituted phthalic anhydride (7) to diamine (8) to 1.98:1 to 2.2:1, preferably 2.0 to 2.1.

After imidization, the bis(phthalimide) (9) is polymerized by reaction with an alkali metal salt of a dihydroxy aromatic compound to provide the polyetherimide (1). In particular, the leaving group X of bis(phthalimide) (9)

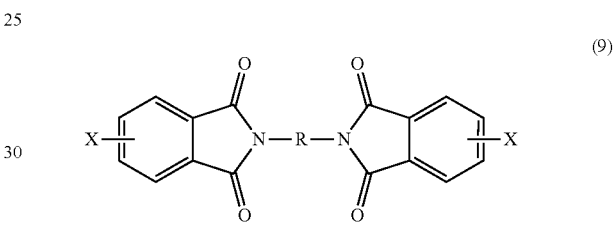

(9)

is displaced by reaction with an alkali metal salt of a dihydroxy aromatic compound of formula (10)

$M^1O—Z—OM^1$ (10)

wherein $M^1$ is an alkali metal and Z is as described in formula (1), to provide the polyetherimide of formula (1)

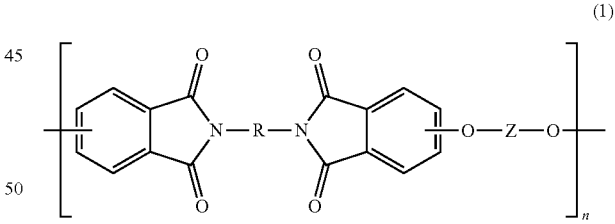

(1)

wherein n, R, and Z are as defined above.

Alkali metal $M^1$ can each independently be any alkali metal, for example, lithium, sodium, potassium, and cesium, and can be the same as $M^2$ (infra). Thus alkali metal salt (10) is lithium salts, sodium salts, potassium salts, cesium salts, and a combination thereof. In some embodiments the metals are potassium or sodium. In some embodiments, $M^1$ is sodium. The alkali metal salt (10) can be obtained by reaction of the metal hydroxide or carbonate with an aromatic dihydroxy compound of formula (4), specifically an aromatic $C_{6-24}$ monocyclic or polycyclic dihydroxy compound optionally substituted with 1 to 6 $C_{1-8}$ alkyl groups, 1 to 8 halogen atoms, or a combination thereof, for example, a bisphenol compound of formula (11)

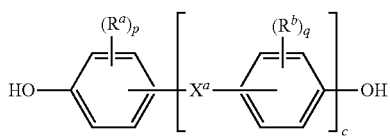

(11)

wherein $R^a$, $R^b$, and $X^a$ are as described in formula (3). In some embodiments, the dihydroxy compound corresponding to formulas (4a) can be used. The compound 2,2-bis(4-hydroxyphenyl) propane ("bisphenol A" or "BPA") can be used.

The polymerization can be conducted in the presence of a capping agent, in particular an alkali metal salt of a monohydroxy aromatic compound of formula (12)

$M^2$-O—$Z^2$ (12)

wherein $M^2$ is an alkali metal and $Z^2$ is derived from a monohydroxy aromatic compound (13) described below. It has been found by the inventors hereof that when the amount of the monohydroxy aromatic salt (12) is greater or equal to 5 mole percent, based on the total moles of the alkali metal salts (10) and (12), a polyetherimide having a weight average molecular weight from more than 200 to less than 43,000 Daltons can be obtained as further described below.

Further, as described in more detail below, the polyetherimides can have low residual content and good physical properties when a capping agent is used. The amount of monohydroxy aromatic salt (12) can be from 0 to 15 mole percent, including up to 15 mole %, or from 3 to 15 mole percent, or from 6 to 15 mole percent, or from 6 to 10 mole percent, based on the total moles of the alkali metal salts (10) and (12). For example, the amount of monohydroxy aromatic salt (12) can be greater than or equal to 5 mole percent to 15, 14, 13, 12, 11, 10, 9, 8, or 7 mole percent.

Alkali metal $M^2$ can be any alkali metal, for example, lithium, sodium, potassium, and cerium, and is generally the same as the alkali metal $M^1$. Thus alkali metal salt (12) is lithium salts, sodium salts, potassium salts, cesium salts, and a combination thereof. In some embodiments, the metals are potassium or sodium. In some embodiments, $M^2$ is sodium. The alkali metal salt (12) can be obtained by reaction of the metal $M^2$ with aromatic $C_{6-24}$ monocyclic or polycyclic monohydroxy compound optionally substituted with 1 to 6 $C_{1-8}$ alkyl groups, 1 to 8 halogen atoms, or a combination thereof, for example, a monohydroxy aromatic compound formula (13)

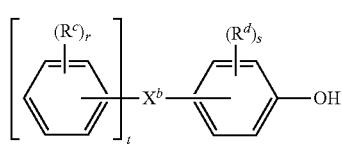

(13)

wherein $R^c$ and $R^d$ are each independently a halogen atom or a monovalent hydrocarbon group, for example a monovalent $C_{1-6}$ alkyl group; r and s are each independently integers of 0 to 4; c is zero to 4; t is 0 or 1; when t is zero, $X^b$ is hydrogen or a $C_{1-18}$ alkyl group; and when t is 1, $X^b$ is a single bond, —O—, —S—, —S(O)—, —S(O)$_2$—, —C(O)—, or a $C_{1-18}$ organic bridging group. The $C_{1-18}$ organic bridging group can be cyclic or acyclic, aromatic or non-aromatic, and can further comprise heteroatoms such as halogens, oxygen, nitrogen, sulfur, silicon, or phosphorous. The $C_{1-18}$ organic bridging group can be disposed such that the $C_6$ arylene groups connected thereto are each connected to a common alkylidene carbon or to different carbons of the $C_{1-18}$ organic bridging group. In some embodiments, t is zero and $X^b$ is hydrogen or a $C_{4-12}$ alkyl group or t is one and $X^b$ is a single bond or a $C_{1-9}$ alkylene group.

For example $Z^2$ is a group of formulas

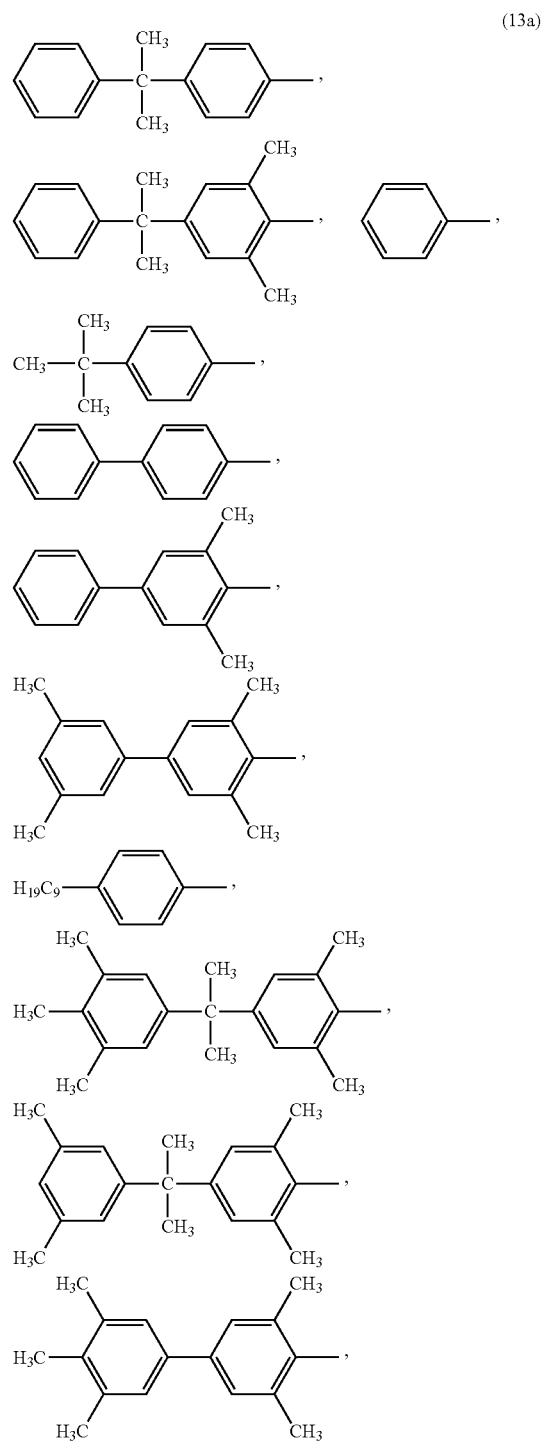

(13a)

or a combination comprising at least one of the foregoing.

In some embodiments, Z and $Z^2$ are each independently a $C_{12-24}$ polycyclic hydrocarbyl moiety optionally substituted with 1 to 6 $C_{1-6}$ alkyl groups. In some embodiments, $M^1$ and $M^2$ are each sodium. For example, Z is a divalent group having formula

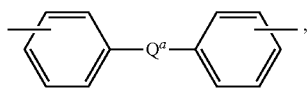

and
$Z^2$ is a monovalent group having formula

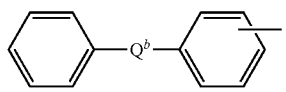

wherein $Q^a$ and $Q^b$ are each independently a single bond, —O—, —S—, —C(O)—, —SO$_2$—, —SO—, —C$_y$H$_{2y}$— wherein y is an integer from 1 to 5, —(C$_6$H$_{10}$)$_z$— wherein z is an integer from 1 to 4; and a halogenated derivative thereof. In other embodiments, $Q^a$ and $Q^b$ are the same, e.g., isopropylidene.

Polymerization by reaction of bis(phthalimide) (9) with a combination of alkali metal salts (10) and (12) can be in the presence of phase transfer catalyst that is substantially stable under the reaction conditions used, in particular temperature. Exemplary phase transfer catalysts for polymerization include hexaalkylguanidinium and α,ω-bis(pentaalkylguanidinium)alkane salts. Both types of salts can be referred to herein as "guanidinium salts."

Polymerization is generally conducted in the presence of a relatively non-polar solvent, preferably with a boiling point above 100° C., specifically above 150° C., for example, o-dichlorobenzene, dichlorotoluene, 1,2,4-trichlorobenzene, diphenyl sulfone, a monoalkoxybenzene such as anisole, veratrole, diphenylether, or phenetole. Ortho-dichlorobenzene and anisole can be particularly mentioned.

Polymerization can be conducted at least 110° C., specifically 150° C. to 275° C., more specifically 175° C. to 225° C. At temperatures below 110° C., reaction rates may be too slow for economical operation. Atmospheric or super-atmospheric pressures can be used, for example, up to 5 atmospheres, to facilitate the use of high temperatures without causing solvent to be lost by evaporation.

In some embodiments, the combination of alkali metal salts (10) and (12) is added directly to the composition containing the bis(phthalimide) (9) in organic solvent. Water removal from the system can be accomplished in either batch, semi-continuous or continuous processes using means known in the art such as a distillation column in conjunction with one or more reactors. In some embodiments, a mixture of water and non-polar organic liquid distilling from a reactor is sent to a distillation column where water is taken off overhead and solvent is recycled back into the reactor at a rate to maintain or increase the desired solids concentration. Other methods for water removal include passing the condensed distillate through a drying bed for chemical or physical adsorption of water.

The molar ratio of the bis(phthalimide) (9) to the alkali metal salt (10) can be 0.9:1 to 1.1:1.0. A solids content of the bis(phthalimide) (9) in the polymerization can be 15 wt. % to 25 wt. %, based on the total weight of the polymerization mixture.

EXAMPLES

The materials in Table 1 were used or made in the following Examples and Comparative Examples.

TABLE 1

| Acronym | Description | Source |
|---|---|---|
| PA | Phthalic anhydride | |
| 3-ClPA | 3-Chlorophthalic anhydride | SABIC |
| 4-ClPA | 4-Chlorophthalic anhydride | SABIC |
| ClPA | Mixture of 3-chlorophthalic anhydride and 4-chlorophthalic anhydride | SABIC |
| ClPAMI | 1,3-bis[N-(4-chlorophthalimido)]-benzene | Examples |
| Mono-ClPAMI (MA) | Mixture of 1-amino-3-N-(4-chlorophthalimido)-benzene, 1-amino-3-N-(3-chlorophthalimido)benzene | Examples |
| mPD | meta-Phenylene diamine | DuPont |
| DDA | 4,4'-diaminodiphenyl sulfone | Atul |
| BPA | 2,2-Bis(4-hydroxyphenyl)propane, (Bisphenol A) | Chiba/CTG |
| BPANa$_2$ | Bisphenol A, disodium salt | SABIC |
| PEI | Polyetherimide | Examples |
| o-DCB | ortho-Dichlorobenzene | Fischer |
| HEGCl or KEG | Hexaethylguanidinium chloride | SABIC |
| SPP | Sodium phenylphosphinate | Akzo |
| PEG | Pentaethylguanidine | Examples |
| NaOH | Sodium hydroxide | Sigma Aldrich |
| KP | Tri-potassium phosphate | Sigma Aldrich |

Property Testing

Weight average molecular weight (Mw) of the polymer product was determined by gel permeation chromatography (GPC) using polystyrene standards. Mz is the z-average molecular weight.

APHA is a single number Yellowness Index used for measuring yellow coloration in nearly white liquid samples. APHA index values were determined in accordance with ASTM D1209. Samples of solutions as reported below were analyzed with a Gretag Macbeth Color Eye 7000A instrument. The instrument readings thus obtained are reported as solution APHA values. In some cases, the solution APHA value was inserted into a formula to yield a calculated estimate of a dry APHA value.

To measure APHA of BPANa$_2$ salt, 2 grams of BPANa$_2$ aqueous solution or oDCB slurry was taken and diluted up to 100 mL using acetonitrile-water mixture (60:40, v/v). After analyzing the sample for APHA using a Gretag Macbeth Color Eye 7000A instrument, the instrument reading was converted APHA based on the dry weight of BPANa$_2$ salt as follows:

$$\text{APHA} = (\text{Solution APHA} \times 100)/(\text{Sample weight} \times \text{solid wt. \%}) \qquad \text{Eq. (1)}$$

All APHA values reported for BPANa$_2$ salt were calculated based on equation (1).

Generally, the solution YI is a number calculated from spectrophotometric data that describes the color of a test sample as being clear or white (low solution YI) versus being more yellow (high solution YI). Sample handling and preparation can affect the test results. The yellowness index of polyetherimide polymer was determined by measuring the solution YI of the resulting solution on a Gretag Macbeth Color Eye 7000A instrument. The instrument reading was referred to as solution YI. The YI values reported and claimed are predicted plaque YI calculated based on the following correlation:

$$\text{Predicted Plaque YI} = (\text{Solution YI} + 18.2)/0.5986 \qquad \text{Eq. (2)}$$

Where indicated, "dry o-DCB" having moisture content of less than 10 ppm was used in the reactions. The dry o-DCB was kept in a glove box over 4-Angstrom molecular sieves.

Gretag Macbeth Color Eye 7000A instrument was used to measure the solution APHA color as well as Yellowness Index (YI) of polymer solution.

General Procedures

BPANa$_2$ Salt Synthesis at Lab Scale

A. BPANa$_2$ Salt Synthesis in Water

Before starting BPANa$_2$ salt synthesis, N$_2$ was bubbled overnight through de-mineralized water (about 1 liter in a round bottom flask) to remove dissolved oxygen. Once the de-oxygenated water was ready, a 4-neck 1-liter round bottom flask was transferred to a glove box (under N$_2$ environment) along with all the raw materials. Then 41.9 grams of BPA, 14.7 grams of NaOH and 449 grams of de-oxygenated water were charged into the RB flask at room temperature, along with a magnetic stirrer, and a condenser was fixed on the top of the flask. The flask was taken to a hood, immersed in an oil bath, and mild magnetic stirring was applied. When the reaction mixture was under mild magnetic stirring, the whole system was then kept under a nitrogen environment for about 30 minutes at room temperature to remove oxygen. Then the oil bath temperature was raised to 70° C. to 80° C. and N$_2$ sweep was provided to maintain inert atmosphere during the course of the reaction. The approximate solid weight % of the BPANa$_2$ salt was around 21%. The system was kept under total reflux conditions to prevent water losses during reaction. Typically after 1 hour the reaction mass became clear, indicating completion of BPANa2 salt formation.

To track the BPANa$_2$ salt quality over time, samples of BPANa$_2$ salt solution were checked at regular time intervals for APHA value and the stoichiometry of the reaction. Based on stoichiometry, corrections were made (either BPA or NaOH) to maintain the desired stoichiometry for BPANa$_2$ salt. The obtained solution APHA was converted on the dry basis based on equation (1). The calculated APHA value is also referred to as APHA of BPANa$_2$ (aqueous stage).

B.: Solvent Swapping into oDCB

Before starting the solvent swapping, oDCB (0.5 to 1 liter) was agitated while applying 150° C. heating oil temperature under N$_2$ sweep for about 0.5 to 1 hour to remove any dissolved oxygen. Aqueous BPANa$_2$ salt solution from step A was added drop wise to oDCB. The aqueous BPANa$_2$ salt solution feed temperature was maintained at about 70° C. to avoid the precipitation of BPANa$_2$ salt, which may create operational difficulties while performing solvent swapping. Water along with the oDCB was collected overhead in the Dean-Stark. Dry ODCB was added to the reactor while water/oDCB was boiled off to maintain the desired percent solids of BPANa$_2$ in oDCB. The total time required for swapping 21 wt. % aqueous BPANa$_2$ salt (100 g batch size) solution was around 5 to 6 hours. After completion of the swapping, the BPANa$_2$ salt solution temperature was increased slowly to 190° C. for the removal of water-oDCB mixture, and maintained until the collected water-oDCB mixture reached a moisture content of 200 to 400 ppm.

C. Homogenization

The oDCB BPANa$_2$ salt slurry was allowed to cool down to room temperature and then transferred to a 1 liter glass bottle under N$_2$ environment. A lab scale IKA homogenizer (Model: T25 Ultra Turrax) was operated intermittently to homogenize the oDCB based BPANa$_2$ salt solution at a speed of 8,000 to 9,000 rpm for about 1 hour (instead of using homogenizer continuously, to avoid local heating, it needed to be switched off after every 15 minutes of use for about 5 to –10 minutes). This homogenization operation was carried out under N$_2$ environment at room temperature.

D. Drying

The homogenized BPANa$_2$ salt was then transferred into either a 1 or 2-liter 5-neck round bottom (RB) flask. For those runs in which tripotassium phosphate (KP) had not been added to BPANa$_2$ salt during the solvent swapping stage, KP in the form of a dry oDCB based slurry with particle size distribution (PSD) of less than 70 micron was then added (1.25 wt. % based on the final polymer weight) at room temperature to the homogenized BPANa$_2$. The 1.25 wt. % excess KP amount was decided based on the observed —OH end group concentration in the final polymer, which should be less than 100 ppm. Particle size of KP was critical to achieve the OH end group specification in the final polymer. N$_2$ was then bubbled through the solution for about 1 to 2 hours at room temperature to remove any oxygen which may have been introduced with the KP slurry or the homogenized BPANa$_2$ salt slurry.

Then the final BPANa$_2$ salt drying was started by adjusting the oil bath temperature to 190° C. to 195° C. The reaction temperature was maintained until the oDCB collected overhead from the system met the water content specification (less than 20 ppm). Then heating was stopped and the BPANa$_2$ salt solution was cooled down to room temperature. Later it was stored under N$_2$ environment inside a glove box at room temperature. Finally the solid percentage of the BPANa$_2$ salt was measured using HCl titration method. Based on this solid wt. % and measured solution APHA of BPANa$_2$, APHA on dry BPANa$_2$ salt basis was calculated. The calculated APHA is also referred to as APHA of BPANa$_2$ (after drying).

BPANa$_2$ Salt Synthesis at Pilot Scale

A. Aqueous BPANa$_2$ Salt Reaction

BPA addition: The required quantity of water to maintain about 25 wt. % of BPANa$_2$ salt was added into an aqueous salt reactor. It was then heated to about 70° C. to 80° C. under N$_2$ bubbling for 2 hours to remove oxygen dissolved in the water. A stoichiometric quantity of BPA was added into the pool of hot water at about 80° C. via hopper in the aqueous reactor.

Caustic lye preparation: The required amount of deoxygenated water to make about 40 wt. % NaOH solution was drained from the aqueous BPANa$_2$ salt reactor prior to BPA addition into a small vessel. The pre-weighed NaOH pellets were added slowly to the small vessel to make caustic lye solution. Preparation of caustic lye solution is an exothermic reaction, so adequate care was taken to minimize the water loss during preparation. The small vessel was cooled with an external ice bath. The caustic lye solution thus prepared was charged into the caustic lye tank which was maintained at room temperature. A continuous N$_2$ bubbling was present through the caustic lye tank until the addition of caustic lye into the aqueous reactor started.

Aqueous reaction: After completion of the BPA addition into the aqueous BPANa$_2$ salt reactor, it was purged with N$_2$ for at least 1 hour to remove any residual oxygen from the reaction mixture. After 1 hour of N$_2$ bubbling, the reactor temperature was decreased to about 70° C. to 74° C. Subsequently the caustic lye tank was pressurized (about 1 to 1.5 barg) and it was charged to BPANa$_2$ reactor over a period of 20 to 30 minutes via a sparger line. As the caustic lye was added, the reactor temperature was allowed to increase by 3° C. to 5° C. due to reaction exotherm. During the initial set of experiments NaOH flakes were charged through a hopper as solid instead of solution. Sufficient care was taken to maintain temperature of the reactor contents below 82° C. by monitoring the rate of NaOH addition. Changing to the addition of lye via sparger helped to minimize the color formation in aqueous BPANa$_2$ salt and also reduced the water loss due to evaporation.

After the completion of NaOH addition, the temperature of the reaction was increased to 80° C. to 85° C. After 1 hour from the completion of caustic lye addition, a sample was removed from the reactor to measure the stoichiometry of the reactant residuals (stoic. specification 97 to 105 mg/L BPA in toluene). If the reaction was not on stoichiometry specification ("on stoic."), corresponding quantities of reactant (BPA or NaOH), as indicated by the BPA salt stoichiometry calculator, was added into the reactor. One hour after the stoic correction, a sample was drawn again and checked for the stoic. The sample was analyzed for APHA to measure the BPANa$_2$ salt color at the aqueous stage. This procedure of sampling, analysis, and stoic correction was repeated until the reaction was on stoic. The on stoic reactor mixture marked the completion of the reaction. The resulting mixture was ready for solvent swapping.

B. Primary Drier (Solvent Swapping) and Homogenization

Once the aqueous BPANa$_2$ salt reaction was considered complete, the aqueous BPANa$_2$ salt reactor was pressurized to about 4 barg and the BPANa$_2$ salt solution was sprayed via spray nozzles into a primary drier (1st drier) containing a pool of hot oDCB at 130° C. to 145° C. The 1st drier was always maintained under N$_2$ purge (about 8 to 10 Kg/hr of N$_2$). As the BPANa$_2$ salt solution was sprayed, free water (unbound water) was quickly evaporated and the BPANa$_2$ precipitated as a white solid in oDCB. During the course of solvent swapping, the quantity of oDCB lost with water due to azeotropic boiling was replaced with fresh oDCB from the dry oDCB storage vessel (earlier oDCB was stored either at 175° C. or 145° C.) so as to maintain a constant percentage solid (13%) of the resulting BPANa$_2$ salt slurry.

After the completion of BPANa$_2$ salt spray, the temperature of the 1st drier was increased to remove the free moisture by stripping of oDCB at its boiling temperature (176° C.). Once the moisture measured in the vapor condensate was decreased to less than 200 ppm, the 1st drier temperature was decreased to 140° C. to 150° C. The BPANa$_2$ salt slurry in oDCB was re-circulated using a pump via a homogenizer (grinder) to reduce the particle size of BPANa$_2$ salt. After 1 hour of homogenization, a pre-homogenized KP slurry in oDCB was pumped into the drier. During the course of homogenization, BPANa$_2$ salt samples were withdrawn and checked for the particle size distribution. The homogenization was continued until the BPANa$_2$ salt particles met the process specification (particle size spec. less than 75 microns), normally at the end of 2.5 hours. The same sample was analyzed for APHA to track the color of the BPANa$_2$ salt.

C. Secondary Drier

The relatively dry slurry (less than 200 ppm moisture) from the 1st stage drier, at about 15% solids, was transferred to a 2nd stage dryer to remove the residual moisture before its use in polymerization. After the transferring of the BPANa$_2$ salt was complete, the temperature of the 2nd stage dryer was increased to 176° C. to remove any bound or unbound moisture from the BPANa$_2$ salt slurry. Again at this stage the oDCB lost due to azeotropic boiling with water was compensated by charging hot dry oDCB from the header into the 2nd drier. During the course of drying, samples were drawn and analyzed for moisture by Karl Fisher titration. Once the BPANa$_2$ salt slurry was dried to less than 20 ppm moisture, the BPANa$_2$ salt slurry was concentrated to a desired level, for example, about 15% by driving off oDCB. After the BPANa2 salt concentration was completed, the temperature of BPANa$_2$ salt slurry was decreased to about 150° C. and stored under nitrogen atmosphere until used in the polymerization step. The concentrated BPANa2 salt slurry sample was withdrawn to measure the BPANa$_2$ salt solid wt. % in oDCB and APHA color. In a further simplification of the process, both drying stages can be conducted in a single drier.

Imidization

A typical ratio of raw materials charged during the course of imidization and then polymerization are provided in Table 2.

TABLE 2

| Raw material | Value | UOM |
|---|---|---|
| mPD/ClPA | 29.6 | % wt. |
| PA/ClPA | 0.9 | % wt. |
| HEGCl/Polymer | 0.8 to 1 | % mol |
| BPA Salt/mPD | 2.5 | kg/kg |

Lab Scale Protocol

Wet oDCB was charged into a reactor, equipped with a mechanical stirrer, a solids addition port, an overhead line with condenser, various addition nozzles, and means to maintain a nitrogen atmosphere. The quantity of oDCB used in a particular reaction was based on the desired percentage solids of the imidization reaction.

After charging oDCB, all the raw materials (mPD, PA and ClPA (95:5 mixture of 4-ClPA and 3-ClPA) were charged into the reactor at room temperature (25° C.). The mixture was kept under continuous nitrogen sweep for an hour to de-oxygenate the system. The temperature of the reaction was then slowly raised to 176° C. in steps within an hour.

Pilot Scale Protocol

After charging oDCB, the temperature of the reactor was increased to about 120° C. During this time oDCB was degassed by bubbling nitrogen through it. When the temperature reached 120° C., ClPA and PA were charged manually through the reactor's hopper. Subsequently the hopper was flushed by oDCB. Next, the temperature of the reactor was increased to about 160° C. over a period of 45 minutes. The reactor was held at this temperature for about 30 minutes to ensure a homogeneous mixture in the reactor. During this time nitrogen was bubbled through the reactant mixture to remove any dissolved gases.

Another vessel was charged with mPD and oDCB at room temperature. The mixture was bubbled with nitrogen for 2 hours, and then heated to 75° C. to 80° C. to provide a solution of mPD dissolved in oDCB (solid wt. %=25 to 27%). The mPD solution thus prepared was charged slowly into the imidization reactor at about 160° C. over a period of 45 minutes. After completion of the mPD addition, the temperature of the reactor was increased to about 170° C. to 175° C. and was held at this condition for the duration of the reaction. During this period, mPD reacted with ClPA to provide oDCB based ClPAMI slurry containing intermediate products of this reaction and water as byproduct. Water vapors leaving the reactor along with oDCB were condensed and collected in the collection pot. At the end of 2 hours, an aliquot sample was drawn to measure the stoichiometry of the reaction. The following species are analyzed for stoichiometry calculations: 4-chlorophthalic acid, 3-chlorophthalic acid, phthalic acid, 4-chlorophthalic anhydride, 3-chlorophthalic anhydride, phthalic anhydride, 4-monoamine, 3-monoamine, and phthalic anhydride monoamine.

The stoichiometry of ClPAMI was calculated using the analysis data for the above chemical species and the appropriate reactant (either ClPA or mPD, referred as stoic correction) were charged to achieve the desired stoichiometry in the imidization reactor. After 1 hour from the completion of stoic correction, a sample was drawn again for measuring the stoic. This activity of sampling and stoic correction was repeated until the desired reaction spec was achieved. Once the reaction was on spec, the ClPAMI was dried to less than 20 ppm moisture in the condensate by stripping of oDCB. The on stoic, dried ClPAMI thus prepared marked the completion of imidization reaction. Generally, the ClPAMI/oDCB slurry was about 13 to 17% solids. Once the moisture specification was achieved, ClPAMI was considered ready for polymerization. The oDCB was continuously distilled out of the system to dry ClPAMI.

The ClPAMI made above was purified by isolating it from the solvent and other soluble impurities, and washed with different solvents or solvent mixture. The solid ClPAMI powder was then dried (at 150° C. under vacuum for 5 to 6 hours) and charged to the polymerization reactor.

Polymerization Process 1

Once the ClPAMI was on stoic then it was dried to achieve less than 20 ppm moisture. Then 1 mole % HEGCl (containing about 500 to 1,000 ppm moisture) was added to ClPAMI and the mixture was dried to less than 20 ppm moisture. Once the dried ClPAMI met all the specs (Stoic: −0.1 to 0.3 mole % ClPA rich, r-MA less than 0.04 mole %), dry BPANa$_2$ salt was added (maintained at 165° C. to 170° C.) over a period of about 30 to 60 min to start the polymerization.

Polymer Isolation and Purification

After the completion of the polymerization reaction, the polymer mass was diluted to approximately 10 wt. % with dry oDCB. A desired amount of H$_3$PO$_4$ (85 wt. % in water) was then added to quench the polymer reaction mass at 165° C. to 170° C. This changed the reaction mass color drastically. Once the reaction mass pH was less than 3, it was assumed that the quenching was done. The total quenching time was about an hour. After quenching, the reaction mass was cooled down to room temperature and passed through vacuum filter assembly to remove the NaCl out of the system. The clear filtrate was then analyzed for solid % and solution Yellowness Index (YI).

Examples 1-4

These examples show that controlling the reaction conditions during polymerization, specifically the wall temperature of the reactor and the agitation rate, affects the final polymer YI and Mz/Mw. The mildest conditions (high speed agitation, and lower hot oil temperature) surprisingly gave a significantly lower YI and a significantly lower Mz/Mw as well. A lower Mz/Mw indicates a polymer that is less branched. When molded, a branched polymer behaves different rheologically than a less branched or unbranched polymer. These differences can negatively affect molding cycle times. Branched polymers may become non-processable if processing conditions were to increase branching even slightly. For example, when a branched polymer is molded at a slightly higher than normal temperature, more branching of the polymer can occur during molding, resulting in a cross-linked part with decreased tensile strength and impact resistance.

Controlled polymerization reactions were performed in a 3 Liter Hastelloy autoclave reactor. All reactions were filtered and washed 2 times. The hot oil temperature, agitation speed and the quality of the BPANa$_2$ were varied as shown in Table 3 for Examples 1-4. The following variables were kept constant during the experiments: ClPAMI source, polymerization procedure (polymerization process 1), final MW of PEI (40-45 kDa), and total reaction time.

TABLE 3

| Example No. | X1: Reaction Conditions[1] | X2: BPA Salt quality[2] |
|---|---|---|
| 1 | + | + |
| 2 | − | + |
| 3 | − | − |
| 4 | + | − |

[1]X1 (−): 1,000 rpm + 190° C. hot oil temperature
[1]X1 (+): 300 rpm + 220° C. hot oil temperature
[2]X2 (−): BPA Salt 100% APHA color 63
[2]X2 (+): BPA Salt 100% APHA color 219

The Mw versus time profiles for Examples 1-4 are shown in FIG. 1. The objective was to reach similar final Mw (40 kDa to 45 kDa) together with a similar cycle time, which for all cases was around 17 hours, so that the results within the runs were comparable.

The detailed reaction conditions as well as raw materials and final analytical results are shown Table 4, wherein "bad" indicates lower salt quality (higher APHA color) and "good" indicates better salt quality (lower APHA color). In Examples 1 and 4, as a result of running at a higher hot oil temperature (wall temperature), the reaction temperature itself increased to a higher value of about 187° C., and the oDCB usage was also much larger, about 4 L/hr instead of less than 1 L/hr, compared to the low temperature cases, namely Examples 2 and 3. Accordingly, the effect on YI and Mz/Mw is a combined effect of reactor wall temperature, agitation speed, and lab reactor conditions that lead to higher reaction temperature and higher oDCB usage.

TABLE 4

| Condition/property | Ex 1<br>Bad BPANa$_2$ +<br>Harsh Condition | Ex 2<br>Bad BPANa$_2$ +<br>Mild Condition | Ex 3<br>Good BPANa$_2$ +<br>Mild Condition | Ex 4<br>Good BPANa$_2$ +<br>Harsh Condition |
|---|---|---|---|---|
| ClPAMI charge (g) | 355.00 | 326.12 | 326.06 | 322.32 |
| ClPAMI stoic (%) | 0.15 | 0.15 | 0.15 | 0.15 |
| BPANa$_2$ color (APHA 100%) | 219 | 219 | 63 | 63 |
| # of stoic corrections | 3 | 2 | 2 | 2 |
| Polymerization time (hr) | 17 | 17 | 17 | 17 |
| Hot oil temperature (° C.) | 220 | 190-195 | 190-195 | 220 |
| Reaction temperature (° C.) | ~187 | ~182 | ~182 | ~187 |
| Agitation (rpm) | 300 | 1000 | 1000 | 300 |
| Quenching temperature (° C.) | 170 | 170 | 170 | 170 |

TABLE 4-continued

| Condition/property | Ex 1<br>Bad BPANa$_2$ +<br>Harsh Condition | Ex 2<br>Bad BPANa$_2$ +<br>Mild Condition | Ex 3<br>Good BPANa$_2$ +<br>Mild Condition | Ex 4<br>Good BPANa$_2$ +<br>Harsh Condition |
|---|---|---|---|---|
| Final % solids | ~25 | ~25 | ~25 | ~25 |
| Estimated boiled oDCB (L/hr) | ~4 | <1 | <1 | ~4 |
| Solids (%) | 6.9 | 6.9 | 7.0 | 6.2 |
| HEG (ppm) | 0 | 0 | 0 | 0 |
| PEG (ppm) | 16 | 13 | 16 | 19 |
| Final Mw (kDa) | 39.8 | 40.0 | 40.8 | 44.9 |
| Mz/Mw | 1.683 | 1.626 | 1.610 | 1.668 |
| Average YI of PEI | 103 | 88 | 82 | 97 |
| St. dev. YI of PEI | 10 | 10 | 3 | 7 |

Figure 2:
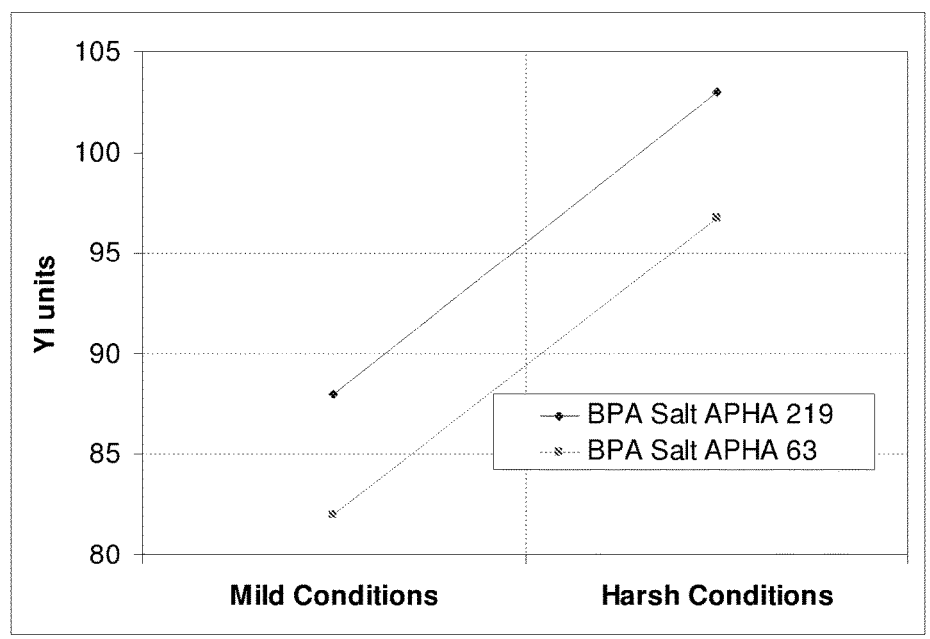
FIG. 2 is a graph of polyetherimide color (YI units) versus conditions (Mild to Harsh).
Figure 3:
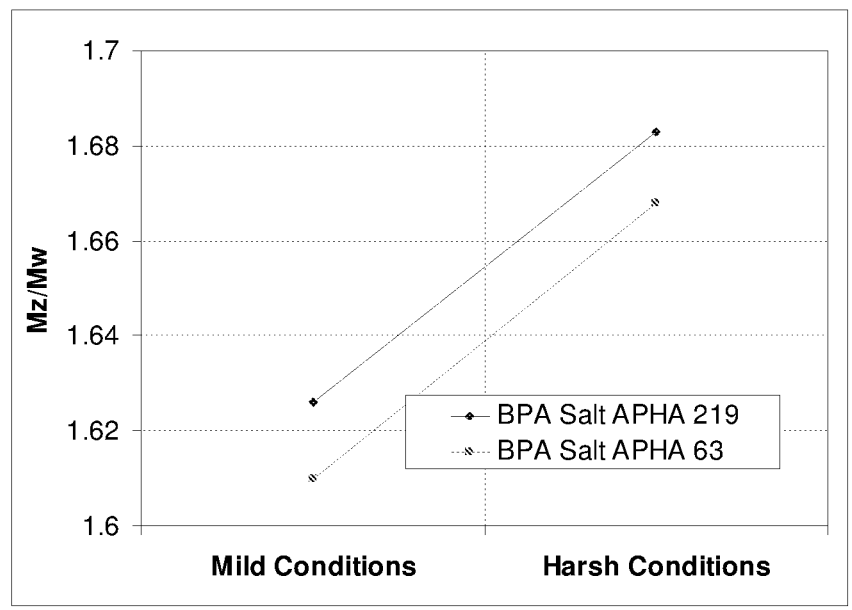
FIG. 3 is a graph of polyetherimide molecular weight (Mz/Mw) versus conditions (Mild to Harsh).

The effects of variables X1 (reaction conditions) and X2 (BPA Salt quality) are also illustrated in FIGS. 2 and 3.

BPA Salt quality effect: +6 YI units/+0.02 Mz/Mw

Reaction conditions effect: +15 YI units/+0.06 Mz/Mw

Examples 5-6

These examples show that phosphoric acid quenching temperature has an impact in YI of the polyetherimide polymer.

Figure 4:
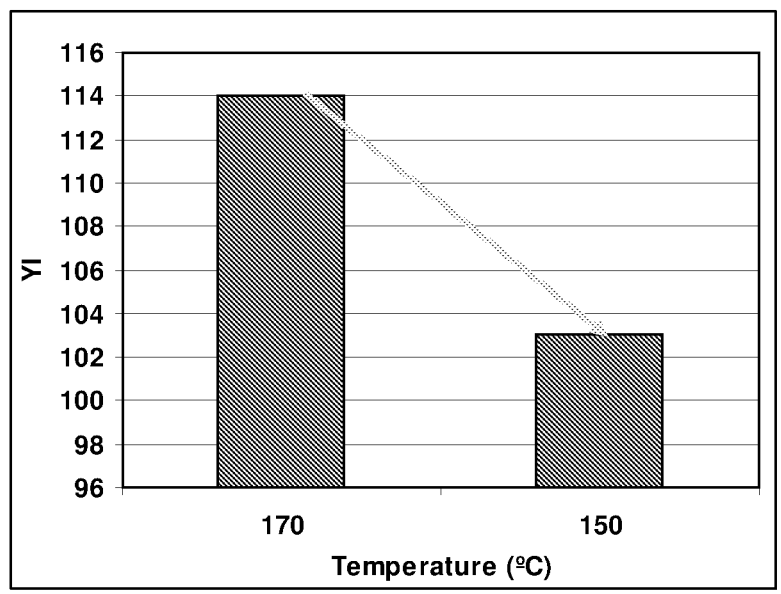
FIG. 4 is a graph of polyetherimide color (YI units) versus temperature (° C.).
Figure 5:
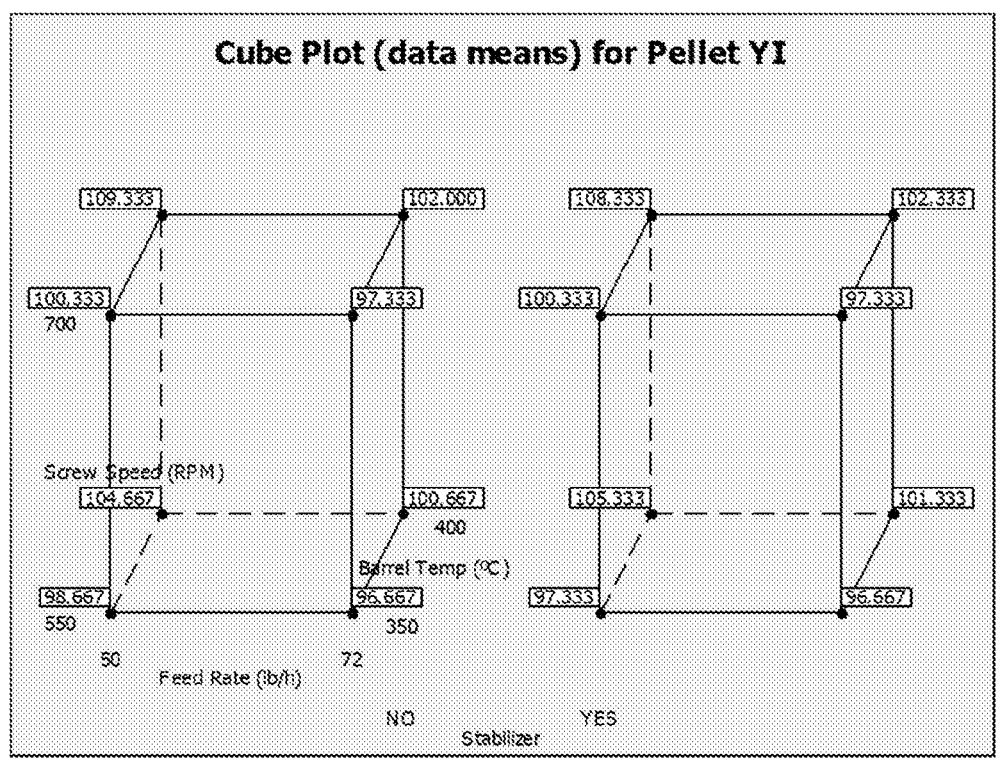
FIG. 5 is a cube plot for analysis of pellet YI for the full factorial design of 4 factors at 2 levels.

Unquenched polymer solution was taken from a master batch prepared according to the general procedure described above. The quenching procedure was followed to achieve pH below 3 using two temperatures, 150° C. and 170° C. The color of the produced PEI was analyzed and the results are shown in Table 5 as well as FIGS. 2-4. The data indicate that there was an improvement of YI by decreasing the quenching temperature from 170° C. to 150° C.

TABLE 5

| Example No. | Quenching temperature (° C.) | YI | L | a* | b* |
|---|---|---|---|---|---|
| Example 5 (1$^{st}$ Run) | 170 | 114 | 79.4 | 9 | 78 |
| Example 5 (2$^{nd}$ Run) | 170 | 114 | 79.8 | 9.6 | 78.7 |
| Average | 170 | 114 | 79.6 | 9.3 | 78.4 |
| Example 6 (1$^{st}$ Run) | 150 | 104 | 82.5 | 4.7 | 71.7 |
| Example 6 (2$^{nd}$ Run) | 150 | 101 | 83.2 | 4.1 | 69.6 |
| Average | 150 | 103 | 80.9 | 7.3 | 75.3 |

These results show that it is possible, using one or all of an oil temperature of 150° C. to 320° C., the disclosed mixing parameters, and the low temperature quenching, to achieve a polyetherimide composition having a YI of less than 93 to 50, or less than 90 to 50, or less than 80 to 50, or less than 70 to 50. The YI is a predicted plaque value that can be determined by dissolving 0.5 grams of polyetherimide in 10 mL of methylene chloride, and measuring the YI of the resulting solution in accordance with ASTM E313; and then converting the value to a predicted plaque YI value using Equation 2 above.

This disclosure is further illustrated by the following Embodiments, which are not intended to limit the claims.

Embodiment 1

A method for the manufacture of a polyetherimide composition, the method comprising: contacting a bis(phthalimide) having the formula

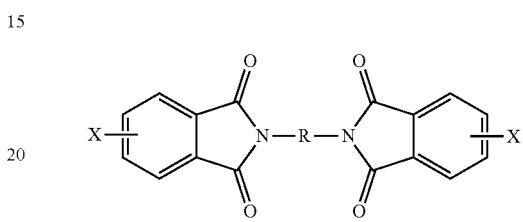

with an alkali metal salt of a dihydroxy aromatic compound having the formula

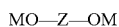

MO—Z—OM in an oil-jacketed reactor, in the presence of a catalyst and 0 to 15%, or 0 to 10% of a capping agent, and at an oil temperature of 150° C. to 320° C., to form a polyetherimide comprising structural units having the formula

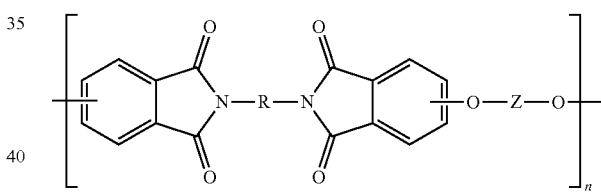

wherein in the foregoing formulae X is fluoro, chloro, bromo, iodo, nitro, or a combination thereof; R is an aromatic hydrocarbon group having 6 to 27 carbon atoms, a halogenated derivative thereof, a straight or branched chain alkylene group having 2 to 10 carbon atoms, a halogenated derivative thereof, a cycloalkylene group having 3 to 20 carbon atoms, a halogenated derivative thereof, —(C$_6$H$_{10}$)$_z$— wherein z is an integer from 1 to 4, an aromatic hydrocarbyl moiety having from 1 to 6 aromatic groups, and a divalent group of the formula

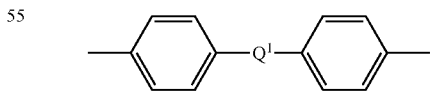

wherein Q$^1$ is —O—, —S—, —C(O)—, —SO$_2$—, —SO—, —C$_y$H$_{2y}$— wherein y is an integer from 1 to 5, or a combination thereof; M is an alkali metal; Z is an aromatic C$_{6-24}$ monocyclic or polycyclic moiety optionally substituted with 1 to 6 C$_{1-8}$ alkyl groups, 1 to 8 halogen atoms, or a combination thereof; and n is an integer greater than 1; and wherein the polyetherimide has a Yellowness Index of from less than 93 to 50.

Embodiment 2

The method of Embodiment 1, wherein the oil temperature is from 180° C. to 240° C.

Embodiment 3

The method of Embodiment 1, wherein the oil temperature is from 188° C. to 192° C.

Embodiment 4

The method of Embodiment 1, wherein the polyetherimide has a Yellowness Index of less than 90.

Embodiment 5

The method of Embodiment 1, wherein the polyetherimide has a Yellowness Index of less than 80.

Embodiment 6

The method of Embodiment 1, wherein the polyetherimide has a Yellowness Index of less than 70.

Embodiment 7

The method of Embodiment 1, wherein the reactor is mixed using an agitator with two sets of pitched turbine blades, with a blade to vessel diameter ratio range of about 0.45 to 0.65, at a speed in a range from about 40 to about 90 revolutions per minute, in a reactor with a volume range from about 20 to 35 cubic meters, and a cylindrical height to diameter ratio range of about 1.3 to about 1.6.

Embodiment 8

The method of Embodiment 7, wherein the agitator has two sets of 45° pitched turbine blades with a blade to vessel diameter ratio of about 0.54 at a speed in a range from about 70 to about 86 revolutions per minute in a reactor with volume of about 28 cubic meters with a cylindrical height to diameter ratio of about 1.45.

Embodiment 9

The method of Embodiment 1, further comprising quenching the polymerization with an acid at a temperature of from 130° C. to 200° C.

Embodiment 10

The method of Embodiment 1, further comprising quenching the polymerization with an acid at a temperature of from 145° C. to 155° C.

Embodiment 11

The method of Embodiment 9, wherein the acid is phosphoric acid.

Embodiment 12

A method for the manufacture of a polyetherimide composition, the method comprising: contacting a bis(phthalimide) having the formula

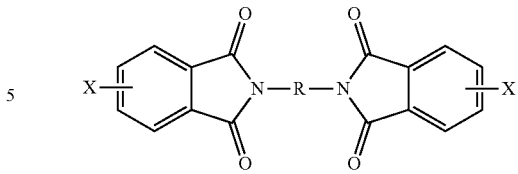

with an alkali metal salt of a dihydroxy aromatic compound having the formula

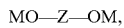

in an oil-jacketed reactor, in the presence of a catalyst and 0 to 10% of a capping agent, and at an oil temperature of 150° C. to 320° C., quenching the polymerization with an acid at a temperature of from 130° C. to 200° C., mixing the reactor using an agitator with two sets of pitched turbine blades, with a blade to vessel diameter ratio range of about 0.45 to 0.65, at a speed in a range from about 40 to about 90 revolutions per minute, in a reactor with a volume range from about 20 to 35 cubic meters, and a cylindrical height to diameter ratio range of about 1.3 to about 1.6, and quenching the polymerization with an acid at a temperature of from 130° C. to 200° C., to form a polyetherimide comprising structural units having the formula

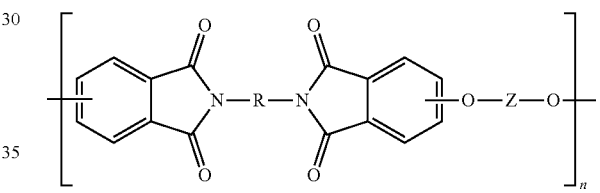

wherein in the foregoing formulae X is fluoro, chloro, bromo, iodo, nitro, or a combination thereof; R is an aromatic hydrocarbon group having 6 to 27 carbon atoms, a halogenated derivative thereof, a straight or branched chain alkylene group having 2 to 10 carbon atoms, a halogenated derivative thereof, a cycloalkylene group having 3 to 20 carbon atoms, a halogenated derivative thereof, $-(C_6H_{10})_z-$ wherein z is an integer from 1 to 4, an aromatic hydrocarbyl moiety having from 1 to 6 aromatic groups, and a divalent group of the formula

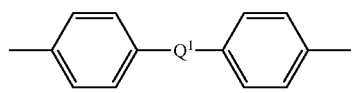

wherein $Q^1$ is $-O-$, $-S-$, $-C(O)-$, $-SO_2-$, $-SO-$, $-C_yH_{2y}-$ wherein y is an integer from 1 to 5, or a combination thereof; M is an alkali metal; Z is an aromatic $C_{6-24}$ monocyclic or polycyclic moiety optionally substituted with 1 to 6 $C_{1-8}$ alkyl groups, 1 to 8 halogen atoms, or a combination thereof; and n is an integer greater than 1; and wherein the polyetherimide has a Yellowness Index of from from less than 93 to 50.

Embodiment 13

The method of Embodiment 12, wherein the polyetherimide has a Yellowness Index of less than 80.

Embodiment 14

The method of Embodiment 12, wherein the polyetherimide has a Yellowness Index of less than 70.

Embodiment 15

The method of Embodiment 12, wherein the agitator has two sets of 45° pitched turbine blades with a blade to vessel diameter ratio of about 0.54 at a speed in a range from about 70 to about 86 revolutions per minute in a reactor with volume of about 28 cubic meters with a cylindrical height to diameter ratio of about 1.45.

In any of the foregoing embodiments,

All molecular weights in this application refer to weight average molecular weights unless indicated otherwise. All such mentioned molecular weights are expressed in Daltons. All ASTM tests are based on the 2003 edition of the Annual Book of ASTM Standards unless otherwise indicated.

The terms "a" and "an" do not denote a limitation of quantity, but rather denote the presence of at least one of the referenced item. "Or" means "and/or." As used herein, "combination thereof" is inclusive of one or more of the recited elements, optionally together with a like element not recited. It is to be understood that any one or more of the described element(s) of the embodiments can be combined in any suitable manner in the various embodiments.

Various numerical ranges are disclosed in this patent application. Because these ranges are continuous, they include every value between the minimum and maximum values. Unless expressly indicated otherwise, the various numerical ranges specified in this application are approximations. The endpoints of all ranges directed to the same component or property are inclusive of the endpoint and independently combinable.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group. The term "alkyl" includes $C_{1-30}$ branched and straight chain, unsaturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, s-pentyl, n- and s-hexyl, n- and s-heptyl, and, n- and s-octyl. The term "aryl" means an aromatic moiety containing the specified number of carbon atoms, such as to phenyl, tropone, indanyl, or naphthyl.

"Substituted" means that the compound or group is substituted with at least one (e.g., 1, 2, 3, or 4) substituents instead of hydrogen, where each substituent is independently nitro (—$NO_2$), cyano (—CN), hydroxy (—OH), halogen, thiol (—SH), thiocyano (—SCN), $C_{1-6}$ alkyl, $C_{2-6}$ alkenyl, $C_{2-6}$ alkynyl, $C_{1-6}$ haloalkyl, $C_{1-9}$ alkoxy, $C_{1-6}$ haloalkoxy, $C_{3-12}$ cycloalkyl, $C_{5-18}$ cycloalkenyl, $C_{6-12}$ aryl, $C_{7-13}$ arylalkylene (e.g, benzyl), $C_{7-12}$ alkylarylene (e.g, toluyl), $C_{4-12}$ heterocycloalkyl, $C_{3-12}$ heteroaryl, $C_{1-6}$ alkyl sulfonyl (—S(=O)$_2$-alkyl), $C_{6-12}$ arylsulfonyl (—S(=O)$_2$-aryl), or tosyl ($CH_3C_6H_4SO_2$—), provided that the substituted atom's normal valence is not exceeded, and that the substitution does not significantly adversely affect the manufacture, stability, or desired property of the compound. When a compound is substituted, the indicated number of carbon atoms is the total number of carbon atoms in the group, including those of the substituent(s).

All references cited herein are incorporated by reference in their entirety. While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

What is claimed is:

1. A method for the manufacture of a polyetherimide composition, the method comprising:

contacting a bis(phthalimide) having the formula

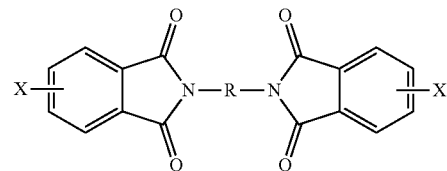

with an alkali metal salt of a dihydroxy aromatic compound having the formula

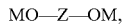

MO—Z—OM, in an oil-jacketed reactor, in the presence of a catalyst and 0 to 10% of a capping agent, and at an oil temperature of 150° C. to 320° C., or 180° C. to 240° C., or 188° C. to 192° C., to form a polyetherimide comprising structural units having the formula

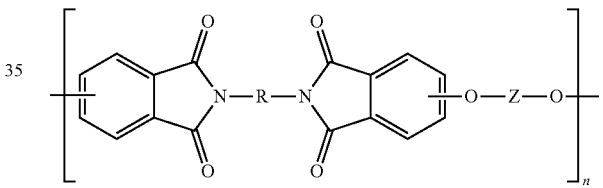

wherein in the foregoing formulae
 X is fluoro, chloro, bromo, iodo, nitro, or a combination comprising at least one of the foregoing;
 R is an aromatic hydrocarbon group having 6 to 27 carbon atoms, a halogenated derivative thereof, a straight or branched chain alkylene group having 2 to 10 carbon atoms, a halogenated derivative thereof, a cycloalkylene group having 3 to 20 carbon atoms, a halogenated derivative thereof, —$(C_6H_{10})_z$— wherein z is an integer from 1 to 4, an aromatic hydrocarbyl moiety having from 1 to 6 aromatic groups, and a divalent group of the formula

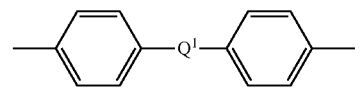

wherein $Q^1$ is —O—, —S—, —C(O)—, —$SO_2$—, —SO—, —$C_yH_{2y}$— wherein y is an integer from 1 to 5, or a combination thereof;
 M is an alkali metal;
 Z is an aromatic $C_{6-24}$ monocyclic or polycyclic moiety optionally substituted with 1 to 6 $C_{1-8}$ alkyl groups, 1 to 8 halogen atoms, or a combination thereof; and
 n is an integer greater than 1; and wherein the polyetherimide has a Yellowness Index of from less than 93 to 50.

2. The method of claim 1, wherein the reactor is mixed using an agitator with two sets of pitched turbine blades, with a blade to vessel diameter ratio range of about 0.45 to 0.65, at a speed in a range from about 40 to about 90 revolutions per minute, in a reactor with a volume range from about 20 to 35 cubic meters, and a cylindrical height to diameter ratio range of about 1.3 to about 1.6.

3. The method of claim 2, wherein the agitator has two sets of 45° pitched turbine blades with a blade to vessel diameter ratio of about 0.54 at a speed in a range from about 70 to about 86 revolutions per minute in a reactor with volume of about 28 cubic meters with a cylindrical height to diameter ratio of about 1.45.

4. The method of claim 1, further comprising quenching the polymerization with an acid at a temperature of from 130° C. to 200° C., or from 145° C. to 155° C.

5. The method of claim 4, wherein the acid is phosphoric acid.

6. The method of claim 1, wherein
X is chloro;
each R is independently a divalent group of formulas

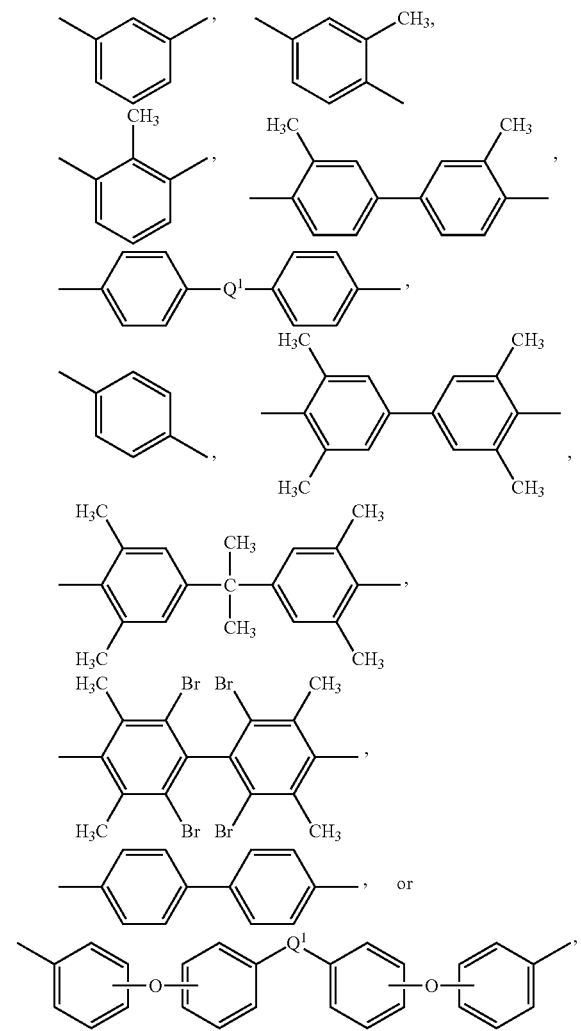

wherein Q' is —O—, —S—, —C(O)—, —SO$_2$—, —SO—, —C$_y$H$_{2y}$— wherein y is an integer from 1 to 5 or a halogenated derivative thereof (which includes perfluoroalkylene groups), or —(C$_6$H$_{10}$)$_z$—
wherein z is an integer from 1 to 4;
Z is a group of the formula

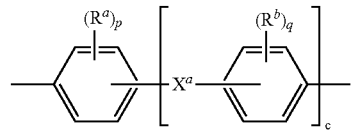

wherein
R$^a$ and R$^b$ are each independently the same or different, and are a halogen atom or a monovalent C$_{1-6}$ alkyl group;
p and q are each independently integers of 0 to 4;
c is 0 to 4;
X$^a$ is a single bond, —O—, —S—, —S(O)—, —S(O)$_2$—, —C(O)—, or a C$_{1-18}$ organic bridging group; and
n is 5 to 500.

7. The method of claim 6, wherein
R is m-phenylene, p-phenylene, bis(4,4'-phenylene)sulfone, bis(3,4'-phenylene)sulfone, bis(3,3'-phenylene)sulfone, or a combination comprising at least one of the foregoing; and
Z is a divalent group of the formula

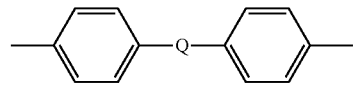

wherein Q is —O—, —S—, —C(O)—, —SO$_2$—, —SO—, or —C$_y$H$_{2y}$— wherein y is an integer from 1 to 5 or a halogenated derivative thereof.

8. The method of claim 7, wherein Q is 2,2-isopropylidene.

9. The method of claim 1, further comprising up to 15 mole % of a capping agent.

10. The method of claim 9, wherein the capping agent is of the formula

M$^2$-O—Z$^2$ wherein
M$^2$ is an alkali metal and
Z$^2$ is derived from a monohydroxy aromatic compound of the formula

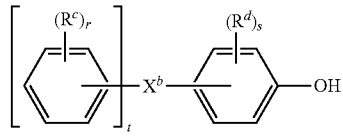

wherein
R$^c$ and R$^d$ are each independently a halogen atom or a monovalent C$_{1-6}$ alkyl group;
r and s are each independently integers of 0 to 4;
c is zero to 4;
t is 0 or 1, provided that when t is zero, X$^b$ is hydrogen or a C$_{1-18}$ alkyl group, and when t is 1, X$^b$ is a single bond, —O—, —S—, —S(O)—, —S(O)$_2$—, —C(O)—, or a C$_{1-18}$ organic bridging group.

11. The method of claim 10, wherein $Z^2$ is of the formula

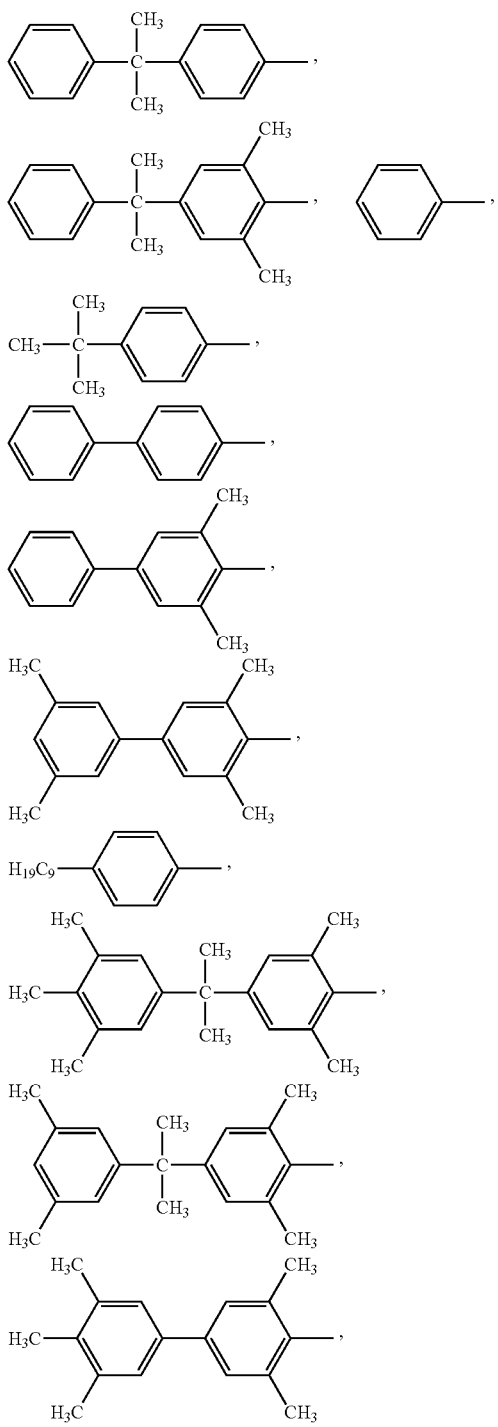

or a combination comprising at least one of the foregoing.

12. The method of claim 1, wherein the contacting the bis(phthalimide) is at an oil temperature of 150° C. to 320° C., in the presence of a catalyst and up to 15 mole % of a capping agent, based on the total moles of the alkali salt the dihydroxy aromatic compound and the capping agent;

the reactor contents are mixed using an agitator with two sets of pitched turbine blades, with a blade to vessel diameter ratio range of about 0.45 to 0.65, at a speed in a range from about 40 to about 90 revolutions per minute, in a reactor with a volume range from about 20 to 35 cubic meters, and a cylindrical height to diameter ratio range of about 1.3 to about 1.6;

the method further comprises quenching the polymerization with an acid at a temperature of from 130° C. to 200° C.; and the polyetherimide has a Yellowness Index of from less than 93 to 50r.

13. The method of claim 12, wherein the agitator has two sets of 45° pitched turbine blades with a blade to vessel diameter ratio of about 0.54 at a speed in a range from about 70 to about 86 revolutions per minute in a reactor with volume of about 28 cubic meters with a cylindrical height to diameter ratio of about 1.45.

14. The method of claim 12, wherein the polyetherimide has a Yellowness Index of from less than 70 to 50.

15. The method of claim 12, wherein the polyetherimide has a Yellowness Index of from less than 80 to 50.

16. The method of claim 12, wherein

R is m-phenylene, p-phenylene, bis(4,4'-phenylene)sulfone, bis(3,4'-phenylene)sulfone, bis(3,3'-phenylene) sulfone, or a combination comprising at least one of the foregoing; and Z is a divalent group of the formula

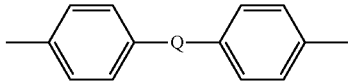

wherein Q is —O—, —S—, —C(O)—, —SO$_2$—, —SO—, or —C$_y$H$_{2y}$— wherein y is an integer from 1 to 5 or a halogenated derivative thereof.

17. The method of claim 16, wherein Q is 2,2-isopropylidene.

18. The method of claim 1, wherein the polyetherimide has a Yellowness Index of from less than 80 to 50.

19. The method of claim 1, wherein the polyetherimide has a Yellowness Index of from less than 70 to 50.

* * * * *